United States Patent [19]

Yeakey et al.

[11] Patent Number: 4,550,184

[45] Date of Patent: Oct. 29, 1985

[54] PRODUCTION OF 2-HYDROXYMETHYL-1,3-DIOXOLANE

[75] Inventors: Ernest L. Yeakey; John R. Sanderson, both of Austin, Tex.

[73] Assignee: Texaco Inc., White Plains, N.Y.

[21] Appl. No.: 683,441

[22] Filed: Dec. 19, 1984

[51] Int. Cl.$^4$ ............................................. C07D 317/00
[52] U.S. Cl. ................................................ 549/453
[58] Field of Search .......................................... 549/453

[56] References Cited

U.S. PATENT DOCUMENTS

| | | | |
|---|---|---|---|
| 2,140,938 | 12/1938 | McNamee et al. | 549/453 |
| 2,862,978 | 12/1958 | Skinner et al. | 549/453 |
| 4,200,765 | 4/1980 | Goetz | 549/449 |
| 4,337,371 | 6/1982 | Kollar | 568/852 |

FOREIGN PATENT DOCUMENTS

| | | | |
|---|---|---|---|
| 1957621 | 5/1971 | Fed. Rep. of Germany | 549/453 |
| 488327 | 7/1938 | United Kingdom | 549/453 |

*Primary Examiner*—Ethel G. Love
*Attorney, Agent, or Firm*—Jack H. Park; Kenneth R. Priem

[57] ABSTRACT

It has been surprisingly discovered in accordance with the present invention that when 1,3-dioxolane is reacted with formaldehyde in the presence of an organic peroxide, the reaction preferentially involves an addition of the formaldehyde to the 2-methylene group of the 1,3-dioxolane with only minor reaction with the 4-methylene and 5-methylene groups of the 1,3-dioxolane whereby the reaction product that is formed contains significant quantities of 2-hydroxymethyl-1,3-dioxolane. 2-Hydroxymethyl-1,3-dioxolane is hydrolyzed with comparative ease to ethylene glycol and the corresponding glycol aldehyde (CHO—CH$_2$—OH). The glycol aldehyde in turn can be catalytically hydrogenated to form additional quantities of ethylene glycol.

9 Claims, No Drawings

PRODUCTION OF 2-HYDROXYMETHYL-1,3-DIOXOLANE

BACKGROUND OF THE INVENTION

1. Technical Field of the Invention

This invention relates to the manufacture of 2-hydroxymethyl-1,3-dioxolane. More particularly, this invention relates to a method wherein 1,3-dioxolane is reacted with formaldehyde in the presence of an organic peroxide under non-acidic conditions to provide 2-hydroxymethyl-1,3-dioxolane. The 2-hydroxymethyl-1,3-dioxolane is useful as a raw material for the manufacture of ethylene glycol.

2. Prior Art

Kollar U.S. Pat. No. 4,337,371 discloses a method for the preparation of ethylene glycol wherein methanol and formaldehyde are reacted in the presence of an organic peroxide and water to provide ethylene glycol. In a technical article Oyama discloses the free-radical reaction of primary and secondary alcohols such as methanol, 2-propanol, ethanol, 2-butanol and 3-methyl-2-butanol with formaldehyde, and t-butyl peroxide to provide glycols (*J. Org. Chem.*, 30, 2429 (1965). Watanabe et al. in an article in *Bull. Chem. Soc. Jpn.*, 56, 1428–1430 (1983), Vol. 56, No. 5 disclose the reaction of 1,3-dioxolane with electron-deficient alkenes such as diethyl maleate, maleic anhydride, etc. Russian Author's Certificate No. 975,704 (Imashev et al.) discloses a method wherein 1,3-dioxolane is oxidized with molecular oxygen at a temperature of about 10° to 60° C. to provide ethylene glycol monoformate as a principle reaction product.

RELATED COPENDING PATENT APPLICATIONS

Copending coassigned Sanderson et al. U.S. patent application Ser. No. 683,549, filed Dec. 19, 1984 (filed of an even date herewith), discloses a method wherein 1,3-dioxolane is oxidized with molecular oxygen to provide 2-hydroperoxy-1,3-dioxolane.

Copending coassigned Sanderson et al. U.S. patent application Ser. No. 683,547, filed Dec. 19, 1984 (filed of an even date herewith), discloses a method wherein 2-hydroxyalkyl-1,3-dioxolanes are prepared by the reaction of 1,3-dioxolane with formaldehyde in the presence of a hydroperoxide and an at least sparingly soluble organic metal salt.

Copending coassigned Yeakey et al. U.S. patent application Ser. No. 683,546, filed Dec. 19, 1984 of an even date herewith), discloses a method wherein dimethoxymethane is reacted with paraformaldehyde in the presence of an organic peroxide to provide an ethylene glycol precursor.

SUMMARY OF THE INVENTION

It has been surprisingly discovered in accordance with the present invention that when 1,3-dioxolane is reacted with formaldehyde under non-acidic conditions in the presence of an organic peroxide, the reaction preferentially involves an addition of the formaldehyde to the 2-methylene group of the 1,3-dioxolane with only minor reaction with the 4-methylene and 5-methylene groups of the 1,3-dioxolane whereby the reaction product that is formed contains significant quantities of 2-hydroxymethyl-1,3-dioxolane. 2-Hydroxymethyl-1,3-dioxolane is hydrolyzed with comparative ease to ethylene glycol and the corresponding glycol aldehyde (CHO—CH$_2$—OH). The glycol aldehyde in turn can be catalytically hydrogenated to form additional quantities of ethylene glycol.

DETAILED DESCRIPTION OF THE INVENTION

Starting Materials

The starting materials for the present invention are 1,3-dioxolane, formaldehyde and an organic peroxide.

Formaldehyde may be employed in its conventional form, as an aqueous formalin solution, in "inhibited" methanol solution as paraformaldehyde, or as trioxane. Formalin is a preferred starting material.

The organic peroxide employed in the process of the present invention is suitably an organic peroxide having the formula:

R—O—O—R'

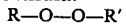

Wherein R and R' are each an alkyl or aralkyl group having 3 to 12 carbon atoms. Organic peroxides which may be employed include, for example, di-tertiarybutyl-peroxide, tertiary-butyl cumyl peroxide, tertiarybutyl ethylbenzyl peroxide, dicumyl peroxide, etc. The preferred organic peroxide is di-tertiarybutyl peroxide.

Reaction Conditions

The desired product of the present invention, 2-hydroxymethyl-1,3-dioxolane, is an equimolar addition product of formaldehyde and 1,3-dioxolane. However, a molar excess of either of the reactants may be used, if desired. Preferably, formalin is used, and is used in a molar excess (e.g., from about 1 to about 5 moles of formaldehyde per mole of 1,3-dioxolane).

The organic peroxide is suitably used in an amount ranging from about 0.1 to about 10 wt. %, based on the 1,3-dioxolane. More preferably, from about 2 to about 5 wt. % of the organic peroxide is used.

The reaction is suitably conducted at a temperature within the range of about 80° to about 250° C., and more preferably, within the range of about 80° to about 150° C.

The reaction is preferably conducted at atmospheric pressure. Superatmospheric or subatmospheric pressures may be used if desired, but there is no particular advantage in doing so.

Reaction times of from about 0.5 to about 10 hours may be employed with satisfactory results. More preferably, the reaction time will be within the range of about 1 to about 5 hours.

The reaction can be conducted in inert solvent solution with a solvent such as acetonitrile, t-butyl alcohol, monochlorobenzene, benzene, etc. but there is no particular advantage in doing so.

At the end of the reaction, the reaction mixture may be separated into components by any suitable technique such as filtration, distillation, solvent extraction, etc.

As indicated earlier, the 2-hydroxymethyl-1,3-dioxolane can be hydrolyzed to provide ethylene glycol and glycolaldehyde under conditions as disclosed, for example in J. D. Roberts, M. C. Caserio, "Basic Principles of Organic Chemistry", W. A. Benjamin, Inc., New York, 1965. See page 443. The glycolaldehyde may also be catalytically hydrogenated to form additional quantities of ethylene glycol under conditions of the type disclosed by H. O. Hause, "Modern Synthetic Reactions", 2nd Ed., W. A. Benjamin, Inc., 1972. See Chapter 1 and references therein.

SPECIFIC EXAMPLES

EXAMPLE 1 (5807-31)

1,3-Dioxolane (80 ml), 17 ml 35% formaldehyde and 3.00 ml tert-butyl perbenzoate were charged to a 300 cc. stainless steel autoclave equipped with magnedrive stirrer. The autoclave was heated slowly (over one hour) to 100° C. and held at 100° C. for two hours. The autoclave was then heated slowly (over one hour) to 130° C. and held at this temperature for one hour. The autoclave was cooled to ambient temperature and the solid paraformaldehyde filtered from the reaction mixture. Most of the unreacted 1,3-dioxolane was removed by distillation at atmospheric pressure. A light yellow oil weighing 19.1 g remained. NMR analysis of the reaction mixture showed the presence of formate (8.1 ppm) and aldehyde (9.7 ppm). A complex variety of bands was observed in the ether region (3.5–5.3 ppm). The light yellow oil was also examined by GC/MS and by CG/FTIR. The results are shown in Table I.

TABLE I

| Compound | Area % | Mass Ion | Abundance | Base Peak |
|---|---|---|---|---|
| Formaldehyde | — | 30 | 50.8 | 29 |
| Water | 30.6 | — | — | — |
| 1,3-Dioxolane | — | 74 | 4.3 | 73 |
| 1,3-Dioxane | — | 88 | 6.2 | 87 |
| Formic acid | 2.3 | 30 | 50.8 | 29 |
| Glycol Aldehyde | 5.1 | — | — | — |
| Ethylene Glycol | 12.1 | 62 | 4.0 | 31 |
| Propylene Glycol | 0.6 | — | — | — |
| Hydroxyethyl Formate | 3.2 | 104 | 0.6 | 31 |
| 1,3-Propanediol | 1.5 | 76 | ~0 | 31 |
| 2-Hydroxymethyl-1,3-dioxolane | 15.8 | 104 | 0.4 | 73 |
| 4-Hydroxymethyl-1,3-dioxolane | trace | — | — | — |
| 2-Hydroxymethyl-1,3-dioxane | 5.8 | 118 | ~0 | 87 |
| Ethylene Carbonate | trace | — | — | — |
| Hydroxypropyl Formate | 1.6 | — | — | — |
| $\left[\begin{array}{c}O\\ \diagdown\\ CH-(CH_2-O)_nH\\ \diagup\\ O\end{array}\right]$ n = 2-5 | 12.2 | — | — | 103 |

Procedure for Experiments Shown in Table II

The procedure for the experiments shown in Table II was essentially the same as 5807-31 except that GC analyses were conducted on unconcentrated reaction mixtures. Details are presented in the table.

TABLE II-A
1,3-DIOXOLANE WITH FORMALDEHYDE

| Notebook Number | 1,3-Dioxolane (g) | Paraformaldehyde (g) | TBHP[a] (ml) | TBPB[b] (ml) | Additive |
|---|---|---|---|---|---|
| 5807-85 | 80.0 | 10.0 | 3.00 | — | — |
| 5807-84 | 80.0 | 10.0 | 3.00 | — | — |
| 5807-83 | 80.0 | 10.0 | 3.00 | — | — |
| 5807-48 | 80.0 | 10.0 | 3.00 | — | — |
| 5831-7 | 80.0 | 10.0 | — | 3.00 | — |
| 5831-8 | 80.0 | 10.0 | — | 3.00 | — |
| 5831-9 | 80.0 | 10.0 | — | 3.00 | — |
| 5831-14 | 80.0 | 10.0 | 3.00 | — | Li$_2$CO$_3$ |
| 5831-15 | 80.0 | 10.0 | 3.00 | — | TSA[e] |
| 5831-16 | 80.0 | 20.0[f] | 3.00 | — | — |

[a] = DTBP = di-tert-butylperoxide
[b] = tert-butylperbenzoate
[c] = Products determined on sample after solid paraformaldehyde had been removed.
[d] = x = 2-5
[e] = Toluene sulfonic acid
[f] = 37% formalin (contains 12.5% methanol)

TABLE II-B
1,3-DIOXOLANE WITH FORMALDEHYDE
Products, (Area %)[c]

| Notebook Number | Time (Hr) | Temp (°C.) | Ethanol | Ethyl Formate | Glycol Ether Acetates | $\left[\begin{array}{c}O\\ \diagdown\\ CHCH_2-OH\\ \diagup\\ O\end{array}\right]$ | $\left[\begin{array}{c}O\\ \diagdown\\ CH(CH_2-O)_n-H^d\\ \diagup\\ O\end{array}\right]$ |
|---|---|---|---|---|---|---|---|
| 5807-85 | 2 | 180 | 4.14 | 16.60 | 1.44 | 8.98 | 3.85 |
| 5807-84 | 3 | 160 | 3.39 | 17.52 | 1.67 | 9.97 | 4.24 |
| 5807-83 | 5 | 140 | 1.46 | 16.16 | 2.09 | 12.10 | 4.07 |
| 5807-48 | 2 | 130 | — | — | — | — | — |
|  | 2 | 140 | 1.48 | 12.11 | 2.17 | 13.94 | 5.06 |
| 5831-7 | 6 | 100 | 0.06 | 3.38 | 1.35 | 16.56 | 4.84 |
| 5831-8 | 4 | 120 | — | 3.85 | 1.19 | 12.98 | 4.65 |
| 5831-9 | 3 | 140 | 1.08 | 5.70 | 1.25 | 12.45 | 3.87 |
| 5831-14 | 5 | 140 | 1.48 | 13.11 | 1.93 | 14.77 | 3.29 |
| 5831-15 | 5 | 140 | 0.15 | 0.05 | 3.75 | 2.48 | 0.93 |
| 5831-16 | 5 | 140 | 4.17 | 4.26 | 1.57 | 6.79 | 1.90 |

[a] = DTBP = di-tert-butylperoxide
[b] = tert-butylperbenzoate
[c] = Products determined on sample after solid paraformaldehyde had been removed.
[d] = n = 2-5
[e] = Toluene sulfonic acid
[f] = 37% formalin (contains 12.5% methanol)

As will be seen from Tables II-A and II-B, good yields of 2-hydroxymethyl-1,3-dioxolane were obtained in all of the runs. Note that when the peroxide that was used was ditertiary butyl peroxide, the yield of 2-hydroxymethyl-1,3-dioxolane was improved through the use of a base such as lithium carbonate to neutralize acidic by-products and that adverse results are experienced when the reaction is conducted under acidic conditions (e.g., 5831-15 where the reaction mixture was acidified with toluene sulfonic acid).

It is also to be noted that with tertiary butyl perbenzoate, there was a greater selectivity to 2-hydroxymethyl-1,3-dioxolane and that significantly smaller quantities of the ethyl formate by-product were produced.

The foregoing examples are given by way of illustration and are not intended as limitations on the scope of the present invention, which is defined by the appended claims.

What is claimed is:

1. A method for the preparation of 2-hydroxymethyl-1,3-dioxolane which comprises reacting 1,3-dioxolane with formaldehyde under non-acidic conditions in the presence of an organic peroxide.

2. A method as in claim 1, wherein the organic peroxide is tertiary butyl perbenzoate.

3. A method as in claim 1, wherein the peroxide is ditertiary butyl peroxide.

4. A method as in claim 3, wherein the ditertiary butyl hydroperoxide is used in combination with a base.

5. A method as in claim 4, wherein the base is lithium carbonate.

6. A method which comprises the steps of reacting 1,3-dioxolane with from about 0.5 to about 5 moles of formaldehyde per mole of dioxolane under basic conditions at a temperature within the range of about 80° to about 250° C. in the presence of from about 0.1 to about 10 wt. % of an organic peroxide, based on the 1,3-dioxolane and recovering 2-hydroxymethyl-1,3-dioxolane from the products of the reaction.

7. A method as in claim 6, wherein the organic peroxide is tertiary butyl perbenzoate.

8. A method as in claim 6, wherein the organic peroxide is ditertiary butyl peroxide.

9. A method as in claim 8, wherein the reaction mixture also includes lithium carbonate.

* * * * *